United States Patent [19]

Olivieri et al.

[11] 4,431,737

[45] Feb. 14, 1984

[54] PROCESS FOR THE PRODUCTION OF ALPHA-GALACTOSIDASE AND USES OF THE ENZYME THUS OBTAINED

[75] Inventors: Roberto Olivieri, Mentana; Paolo Pansolli, Rome; Eugenio Fascetti, Rome; Pierluigi Ciuffolotti, Rome, all of Italy

[73] Assignee: Anic, S.p.A., Palermo, Italy

[21] Appl. No.: 445,844

[22] Filed: Nov. 30, 1982

[30] Foreign Application Priority Data

Dec. 3, 1981 [IT] Italy ................................ 25424 A/81

[51] Int. Cl.³ .......................... C12N 9/40; C12N 1/18; C13J 1/00; C12R 1/865
[52] U.S. Cl. .................................... 435/208; 435/256; 435/276; 435/942; 426/46
[58] Field of Search ............... 435/256, 208, 276, 942; 426/46

[56] References Cited

U.S. PATENT DOCUMENTS 4,008,334  2/1977  Hansen .................................. 426/46
4,216,235  8/1980  Dasek et al. ......................... 426/46

OTHER PUBLICATIONS

Chemical Abstracts, vol. 84:103854v (1976) Abstract of Japan Kokai 75 63,187 (Suzuki et al.).
Chemical Abstracts, vol. 91:73290h (1979).
Chemical Abstracts, vol. 93:41179d (1980).

Primary Examiner—Lionel M. Shapiro
Attorney, Agent, or Firm—Hedman, Gibson, Costigan & Hoare

[57] ABSTRACT

The enzyme alpha-galactosidase is prepared from a constitutive mutant of the strain *Saccharomyces cerevisiae* NRRL-Y-12057, said mutant being marked by the identification number NRRL-Y-12533.

8 Claims, No Drawings

PROCESS FOR THE PRODUCTION OF ALPHA-GALACTOSIDASE AND USES OF THE ENZYME THUS OBTAINED

This invention relates to a process for the production of the enzyme alpha-galactosidaze (E.C. 3.2.1.22) by culturing a mutant of the strain Saccharomyces cerevisiae NRRL-Y-12057 and relates also to the hydrolysis of the oligosaccharides raffinose and stachyose by employing the same enzyme.

The trisaccharide raffinose which is present in fair amounts in sugar beets hinders the crystallization of sucrose and consequently lowers the extraction yields.

This circumstance is a serious economical problem for sugar mills and the hydrolysis of raffinose is consequently required in order to improve both the quantitative yield and the efficiency of the crystallization process of the extracted sugar.

Many papers describe enzymic processes for the hydrolysis of raffinose by exploiting enzymes extracted from a number of species of microorganisms of the genera Absidia, Aspergillus, Bacillus, Circinella, Escherichia, Micrococcus, Mortierella, Penicillium and others (see for example the U.S. Pat. Nos. 3,647,625 and 3,767,526).

However, when culturing many microoganisms, the cellular extract does contain not only alpha-galactosidase, but also invertase, so that, during the treatment of sugar beet molasses, the enzymic hydrolysis of raffinose is accompanied by the undesirable hydrolysis of sucrose also.

It is likewise known that soybeans are an important source of proteins as used in the preparation of a number of foodstuffs for human use.

The presence, in soybean meal, in particular, of high amounts of stacyose and raffinose sets stringent limitations to a mass-production applications when formulating food products. As a matter of fact, such sugars cannot be digested by human beings due to the absence of the alpha-galactosidase enzyme and cannot even be degraded by the intestinal mucous membranes, but their fermentation is brought about, instead, by the intestinal microorganism flora so that flatulence may occur, often accompanied by diarrhoea. The same troubles are experienced in the assimilation of soybean milk which is quite an acceptable substitute for cow's milk, especially for those systems which exhibit intolerance towards ordinary milk due to the inability of digesting lactose.

It has now been found that the degradation of oligosaccharides and monosaccharides both in soybean meal and soybean milk by employing S. cerevisiae cells (cell extract or the purified enzyme) offsets flatulence and imparts a high economical value to the product.

An object of the present invention, in fact, is to provide a novel constitutive mutant of the strain Saccharomyces cerevisiae NRRL-Y-12057 described in the U.S. Pat. application Ser. No. 213,657 filed on Dec. 5, 1980, said mutant producing high amounts of alpha-galactosidase, absolutely exempt from invertase irrespective of the addition of galactose to the culturing media, galactose being conversely essential for inducing an adequate activity level of the alpha-galactosidase in the fermentations of the wild strain.

Furthermore, inasmuch as the enzymic activity which is the subject matter of this invention finds an application in processes for the preparation of foodstuffs, it is essential that the microorganism which is to be used is generally recognized as safe, as is just the case with S. cerevisiae, differently from many other microorganisms which have been described as producers of alpha-galactosidase.

The microorganism which is the subject matter of the present invention has been obtained by subjecting to the action of ultraviolet radiations and for an appropriate time a population of S. cerevisiae, var. oleaginosus NRRL-Y-12057. The colonies formed on an agar-agar containing culturing nutrient medium by the microorganisms which have survived the mutant-producing treatment have been analyzed to ascertain their ability to produce alpha-galactosidase activity in culturing media from which galactose had been excluded.

By adopting such a procedure, a clone has been isolated which is capable of reusing high amounts of alpha-galactosidase also when no inductor is present. This novel microorganism has been deposited on Sept. 7, 1981 with the Northern Regional Center U.S. Department of Agriculture, Peoria (ɔ 12) where it has been allotted the identification symbol NRRL-Y-12533.

A few physiological characteristics of said strain are tabulated hereunder and compared with those of the corresponding wild strain (NRRL-Y-12057).

1. Utilization of the carbon sources.

|  | NRRL-Y-12057 | The mutant |
|---|---|---|
| (a) Fermentation | | |
| Glucose | + | + |
| Galactose | + | + |
| Maltose | + | + |
| Melibiose | + | + |
| Raffinose | + | + |
| Threalose | − | − |
| (b) Assimilation | | |
| Glucose | + | + |
| Galactose | + | + |
| Maltose | + | + |
| Threalose | ± | ± |
| Raffinose | ± | + |
| Melibiose | + | + |
| D-mannitol | − | − |
| Glycerol | ± | ± |
| Ethanol | ± | ± |
| DL-lactic acid | − | − |

2. Production of alpha-galactosidase.

| Galactose° in culturing medium | Specific activity (Units/dry weight) | |
|---|---|---|
| | NRRL-Y-12057 | Mutant |
| 1 gram/liter | 2200 | 11000 |
| − | 200 | 11000 |

°The basic culturing medium was composed of glucose 10 g/l, urea 2 g/l, NaH$_2$PO$_4$ 2 g/l, MgSO$_4$.7H$_2$O 0.5 g/l, yeast extract 2 g/l (grams per liter).

A culturing medium for the production of alpha-galactosidase from the mutant contains an assimilable carbon source, a nitrogen source and mineral salts.

Glucose, melibiose, glycerol and galactose can be used as carbon sources. Corn steep liquor, yeast extract, meat extract, casein hydrolyzates, soybean meal, ammonium salts and urea can be used as nitrogen sources.

An appropriate culturing medium, for example, may have the following composition:
Corn steep liquor: 20 g/l (grams per liter)
Glucose: 10 g/l
NaH$_2$PO$_4$: 2 g/l
MgSO$_4$.7H$_2$): 0.5 g/l The pH range for such a culturing medium is between 4 and 7, and preferably between 5 and 6, the temperature is from 20° C. to 40° C., and preferably between 25° C. and 30° C.

The duration of the fermentation can be varied between 16 and 72 hours, and the range from 30 to 40 hours is preferred.

The cells which are collected on completion of the fermentation run may be used as such or in the form of a dry powder. As an alternative, raw or purified extracts from such cells may also be used.

To this purpose, the cells are ruptured with any of the conventional methods and the raw or the purified extract, which contains the enzyme, is used.

Lastly, an additional technical and economical improvement may be adopting by immobilizing the enzyme by combination of it with macromolecular compounds, by formation of chemical bonds with the carrier, or bonds of ionic type, or also by physical immobilization of the enzyme or the cells.

The examples to follow make conspicuous other modes of operation in connection with the present invention, but they are not limitations thereto.

EXAMPLE 1

A culturing broth is prepared, having the following composition:
Glucose: 10 g/l
Corn steep liquor: 20 g/l
$NaH_2PO_4$: 2 g/l
$MgSO_4.7H_2O$: 0.5 g/l pH: 6.0 (with NaOH)

Portions of 100 mls each of the medium so prepared have been distributed in 500-ml flasks and sterilized for 30 minutes at 116° C. The flasks so prepared were inoculated with a culture of the strain *S. cerevisiae* grown for 48 hours at 30° C. on Potato Dextrose Agar Slants. (Difco). After a 48-hour incubation at 30° C. with orbital stirring at 220 rpm, the biomass was collected by centrifuging the broth culture. From 100 mls of broth there were obtained 600 mg of dry microbial cells, containing 11,000 units of alpha-galactosidase per gram.

The enzymic activity of the moist paste was determined as indicated hereinafter.

A 37% solution of raffinose pentahydrate (weight/volume ratio) was prepared in a 0.1 M, pH 5.0 sodium acetate buffer.

To 100 mls of a solution so prepared and previously incubated in a thermostatically controlled (40° C.) stirrer there was added 1 g of moist cells. Starting from the 0 time and at 10-minute intervals, there was drawn 0.5 ml of the reaction mixture, to be added to 10.5 mls of 0.01-normal HCl. The suspension so obtained was centrifuged to remove the biomass, and the galactose contents was measured on the clear supernatant according to the Boehringer Mannheim Lactose-Galactose Testing Method.

A test made according to the procedure outlined above has given the following results:

| Reaction times minutes | Produced Galactose (micromols in the sample) |
|---|---|
| 0 | 166 |
| 10 | 538 |
| 20 | 888 |
| 30 | 1,227 |
| 40 | 1,711 |
| 50 | 1,955 |
| 60 | 2,222 |

If a unit is defined as the quantity of enzyme which produces, under the test conditions outlined above, one micromol of galactose in one hour, the result is that one gram of cellular paste contained 2,056 units of alpha-galatosidase. Inasmuch as the contents of dry matter in the tested cellular paste was 18.7% of its moist weight, the activity per gram of dry microbial cells was equal to 11,000 units.

EXAMPLE 2

Hydrolysis of raffinose in the "low greens" of crystallization of sucrose.

The hydrolysis of raffinose was carried out in the "low greens" of crystallization of sucrose (raw sugar) coming from the sugar mills of Celano (L'Aquila, Italy), the liquors having the following composition:
Dry matter contents: 65–70 Bx
Percentage composition on the dry matter basis:
Sucrose: 68%
Raffinose: 1.8%
Non-sugars: 30%

A quantity (0.5 kg) of these "greens" has been adjusted to a pH of 5 by adding thereto 5 ml of conc. sulfuric acid and introduced into a flask, the latter being shaken in a shaker, thermostatically controlled at 40° C.

The hydrolysis of raffinose started upon addition of 5 g (dry basis weight) of cellular biomass as prepared according to EXAMPLE 1. At time intervals, samples have been drawn from the flask to determine the galactose contents (Enzymic method Boehringer Mannheim Lactose-Galactose Test) as produced by enzymic hydrolysis of the raffinose. The kinetic trend of the reaction has been monitored until 60% of the total raffinose contents had been hydrolyzed.

After 0.5, 1.5, 3, 5, 8 and 12 hours, the percent of hydrolyzed matter was 10%, 20%, 30%, 40%, 50% and 60%, respectively.

EXAMPLE 3

Hydrolysis of stachyose and raffinose in soybean meal.

A quantity (0.7 kg) of soybean meal (ADM-TNF-40) was introduced in a powder blender (DEMACO) and 0.2 liter of water added thereto.

Due to the mixing effect, a homogeneous doughlike mass was obtained, to which there were added 160 g of cellular biomass (moist weight) prepared as described in EXAMPLE 1.

After 1-hour blending at a temperature of 40° C., a sample (12 g) was withdrawn, from which carbohydrates were removed with 200 mls of a 70/30 mixture of ethanol and water. The extraction was repeated thrice, whereupon the extract was acidified and separated from the solids by centrifugation.

The supernatant was concentrated in vacuum to 400 mls. A similar extraction was carried out on a soybean meal sample (the blank) which had been subjected to the same treatment but without adding any biomass thereto.

The quantitative analysis of the sugars (stachyose-raffinose-sucrose) was carried out in a liquid chromatograph operating under pressure (Hupe and Busch 1010B) working under the following conditions.

Eluant H₂O/CH₃CN (30/70); Column: 2 Hibar NH₂ (Merck); Flow: 2 ml/minute; Pressure 150 atm.

The sugar contents in the soybean meal (blank) which had not been treated with the cells displaying the enzymic activity was, in terms of percentage: Stachyose: 5.5%—Raffinose: 1.5% and Sucrose: 6%, whereas, in the meal which had been treated with the enzyme for 1 hour, it was: Stachyose: 0.1%—Raffinse: 1% and Sucrose: 9.2%.

EXAMPLE 4

Hydrolysis of stachyose and raffinose in soybean milk.

10 g of soybean meal (ADG-TNF 40) have been slurried in 200 mls of water and heated to a boil. The slurry thus obtained was centrifuged for 5 minutes at 5,000 rpm to separate the insoluble residue from the supernatant solution, the latter being the so-called soybean milk. One half of this solution was introduced in a flask kept stirred in a 40° C. thermostatic bath and 0.5 g of moist cells of *Saccharomyces cerevisiae* (dry weight 100 mg) was added thereto. After 4-hour incubation, the mixture was centrifuged and, on a 50-ml portion the oligosaccharide contents was determined quantitatively. A similar determination was made on the same volume of soybean milk which had not been treated with the microbial cells (blank).

Both to the blank and the sample there were added 120 mls of abs. ethanol, that which brought about the formation of a proteinic precipitate which was separated by filtration from the solution: the latter was restored to its initial volume of 50 mls by evaporation under vacuum. Portions of 20 microliters each were injected into a liquid-pressure chromatograph (Hupe and Bush 1010 B) for the quantitative determination of the sugars as described in the previous Example.

The results, expressed in terms of mg of oligosaccharides per 100 mls of soybean milk were as follows:

|  | Raffinose | Stachyose | Total | % Hydrolysis |
| --- | --- | --- | --- | --- |
| Blank | 60 | 220 | 280 | 0 |
| Treated milk | 45 | 50 | 95 | 66 |

We claim:

1. A biologically pure culture of *Saccharomyces cerevisiae* NNRL-Y 12533, said culture being capable of producing alpha-galactosidase in the absence of galactose.

2. A method for the preparation of the microorganism claimed in claim 1, consisting in subjecting to the action of ultraviolet radiations the microorganism of the *Saccharomyces cerevisiae* genus, variety *oleaginosus* identified by the symbol NRRL-Y-12057.

3. Method for the preparation of alpha-galactosidase comprising the step of culturing the *Saccharomyces cerevisiae* NRRL-Y-12533 strain in a culturing medium containing enzyme-inducing substances and recovering the alpha-galactosidase thus produced.

4. Method according to claim 3, wherein the inducing substances are members selected from the group consisting of glucose, melibiose and galactose.

5. Method according to claim 3, wherein the fermentation is carried out in a pH range of from 4 to 7.

6. Method according to claim 3, characterized in that the fermentation is carried out at a temperature comprised between 20° C. and 40° C.

7. Method for the preparation of alpha-galactosidase comprising the step of culturing strain NRRL-Y-12533 of *Saccharomyces cerevisiae* in a culturing medium that is free of an inductor and thereafter recovering the alpha-galactosidase thus produced.

8. A biologically pure culture of *Saccharomyces cerevisiae* NRRL-Y-12533.

* * * * *